United States Patent [19]

Vickery

[11] Patent Number: 4,553,972
[45] Date of Patent: Nov. 19, 1985

[54] DISPOSABLE INTRAVAGINAL CONTRACEPTIVE DEVICES RELEASING 1-SUBSTITUTED IMIDAZOLES

[75] Inventor: Brian H. Vickery, Cupertino, Calif.
[73] Assignee: Syntex (U.S.A.) Inc., Palo Alto, Calif.
[21] Appl. No.: 496,729
[22] Filed: May 20, 1983
[51] Int. Cl.$^4$ .............................................. A61M 31/00
[52] U.S. Cl. ...................................... 604/892; 128/127
[58] Field of Search ................ 604/892, 893; 128/127, 128/130, 131, 132

[56] References Cited

U.S. PATENT DOCUMENTS 3,991,760 11/1976 Drobish et al. ...................... 128/127
3,995,633 12/1976 Gougeon ............................. 128/127
4,198,976 4/1980 Drobish et al. ...................... 604/892
4,215,691 8/1980 Wong .................................. 604/892
4,304,226 12/1981 Drobish et al. ...................... 128/127
4,311,543 1/1982 Strickman et al. .................. 128/127

Primary Examiner—C. Fred Rosenbaum
Assistant Examiner—Christa K. Scott
Attorney, Agent, or Firm—Annette M. Moore; Tom M. Moran

[57] ABSTRACT

Devices, of suitable form and size for insertion into the vagina of a female mammal, composed of a polymeric material which has, incorporated in it, a 1-substituted imidazole spermicide and a pharmaceutically acceptable chelating agent, and which release effective amounts of said spermicide while in place in the vaginal cavity, are useful as contraceptives.

15 Claims, 5 Drawing Figures

DISPOSABLE INTRAVAGINAL CONTRACEPTIVE DEVICES RELEASING 1-SUBSTITUTED IMIDAZOLES

BACKGROUND OF THE INVENTION

The present invention relates to methods and devices for contraception which depend upon spermicidal activity of 1-substituted imidazoles applicable to the female mammal intravaginally. More specifically, the present invention concerns intravaginal inserts, such as diaphragms, rings, or cervical caps which contain, within the matrix of the material of which they are composed, a spermicide of the chemical class of 1-substituted imidazoles and a pharmaceutically acceptable chelating agent, and which devices are capable of releasing an effective amount of said spermicide at a controlled rate in situ.

Present methods of contraception suffer from a variety of well known defects. Systemically active drugs which alter the ovulatory cycle of the female, whether taken orally, or inserted in the uterus or vagina for slow release, cause a substantial number of side effects ranging from discomfort and menstrual irregularities to life threatening alterations in metabolism. Mechanical barriers, such as condoms and diaphragms, in their present form, are not ideally effective, and, more importantly, do not have maximum user acceptance because of the necessity of their being employed in the same psychological time frame as intercourse. Spermicidal preparations designed for intravaginal application are even less effective and less aesthetically acceptable than the aforesaid mechanical barrier devices. The goal of a contraceptive which is (a) effective (b) confined in its metabolic effects to contraception itself, and (c) can be employed at a time far psychologically removed from the sex act, has not been achieved in the prior art.

Intravaginal devices for release of contraceptive materials are well known, and many designs have been described: for example, a vaginal contraceptive tampon is described in international application published under No. PCT 80/00008 (claiming priority from U.S. application Ser. No. 888,578); a vaginal medicator in U.S. Pat. No. 3,885,564; a vaginal ring in U.S. Pat. No. 3,545,439; a diaphragm in U.S. Pat. No. 2,087,610, and a cervical cap in U.S. Pat. No. 2,836,177.

Devices for the release of a progestational agent as the active ingredient have also been described: (WHO Special Programme of Research, Development and Research Training in Human Reproduction, Geneva, Switzerland: *Journal of Steroid Biochemistry* 11 (1B) 461 (1979); Burton, F. G., et al, *Contraception* 17 (3) 221 (1978); Gordon, N. R., et al, *Saf. Health Plast. Nat'l. Tech. Conf. Soc. Plast Engr.* 1977, 109. Victor, A., et al, *Contraception*, 16 (2) 125 (1977), Zanartu, et al, *Steroids* 21 (3) 325 (1973); British patent application No. 2,616,064. However, the results have been unsatisfactory because of continuing problems with unwanted metabolic alterations and because of the difficulty of assuring proper release of the steroid (WHO study, supra). As systemic contraceptives, progestational compounds are subject to causing such side effects regardless of the mode of administration.

Release of spermicides, because the effect is not systemic to the female host, is an inherently more desirable option. Devices which release spermicides of the surfactant type have also been described: Stone, et al, *Am. J. Obstet. and Gynecol.* 133 (6): 635 (1979), U.S. Pat. No. 4,031,202, British Pat. No. 1,329,619, European Pat. Nos. 9-417 and 9-518. However, surfactant spermicides are effective only at relatively high concentrations, and devices which remain in the vaginal cavity are incapable of releasing effective amounts over long periods. Furthermore, surfactants are not effective within the cervical mucus. Hence, effectiveness is impaired because the critical sperm pathway through the mucus to effect conception remains unimpaired.

The present invention utilizes 1-substituted imidazole spermicides and a pharmaceutically acceptable chelating agent. Because of the effectiveness of these spermicides at low concentrations, intravaginal devices which incorporate them and a pharmaceutically acceptable chelating agent into the matrix of the device are capable of releasing effective quantities for a prolonged period to be absorbed by the cervical mucus. The devices and method of this invention thus permit a method of contraception which is esthetically more appealing and provides greater protection than the above known methods.

SUMMARY OF THE INVENTION

The present invention concerns a device of suitable configuration for vaginal insertion and long term retention in the female mammal, which is composed of an inert flexible polymeric material wherein the polymerization is effected in the presence of a 1-substituted imidazole spermicide or their pharmaceutically acceptable acid addition salts and a pharmaceutically acceptable chelating agent and wherein the resulting polymer is permeable to the release of said spermicide and chelating agent.

This device is useful for effecting contraception. Accordingly, another aspect of the present invention concerns a method of contraception using said device and a method of contraception including removing the device prior to coitus.

DETAILED DESCRIPTION

Definitions:

As used herein:

"Spermicide" or "spermicidal" includes those agents which kill sperm, and also those which otherwise immobilize or render sperm ineffective in fertilization;

"Inert" means material which does not dissolve in, or become absorbed by, the fluids or structures of the vaginal cavity, and maintains its structural and configurational integrity in the vaginal environment;

The term "pharmaceutically acceptable chelating agent" refers to those chelating agents which do not have a deleterious effect on the subject using the composition.

"Alkyl" refers to a branched or unbranched saturated hydrocarbon substituent containing two to twelve carbon atoms, such as, for example, ethyl, i-propyl, n-butyl, n-hexyl, n-octyl or n-dodecyl.

"Lower Alkyl" refers to a straight or branched chain monovalent substituent consisting solely of carbon and hydrogen containing no unsaturation and having one to four carbon atoms. Examples of lower alkyl are methyl, ethyl, i-propyl, n-propyl, n-butyl, i-butyl and t-butyl.

"Cycloalkyl" refers to a cyclic saturated monovalent substituent consisting solely of carbon and hydrogen and having five to seven carbon atoms in the ring. Examples of cycloalkyl are cyclopentyl, cyclohexyl and cycloheptyl.

"Cycloalkylalkyl" refers to a cycloalkyl group as defined above attached to an alkylene chain of one to three carbon atoms. Non-limiting Examples of cycloalkylalkyl groups are cyclopentylmethyl, cyclohexylethyl and cyclohexyl-n-propyl.

"Alkenyl" refers to a straight or branched chain monovalent substituent of two to twelve carbon atoms consisting solely of carbon and hydrogen containing olefinic unsaturation. Examples of alkenyl are ethenyl, n-butenyl, n-pentenyl, i-pentenyl, n-octenyl and n-dodecenyl. "Lower alkenyl" refers to alkenyl of two to four carbon atoms. Examples of "lower alkenyl" are ethenyl, propenyl and butenyl.

"Phenyl-lower-alkyl" refers to phenyl ring attached to an alkylene chain of one to four carbon atoms. Examples of "phenyl-lower-alkyl" are benzyl, phenylethyl and 4-chlorophenylpropyl. "Phenyl-lower-alkenyl" refers to phenyl ring attached to a lower alkenylene chain. Examples of "phenyl-lower-alkenyl are phenylethenyl, phenylpropenyl and 4-methoxyphenylbutenyl.

"Lower alkoxy" refers to OR" wherein R" is lower alkyl as defined above. Examples of "lower alkoxy" are methoxy, ethoxy and i-propoxy.

"Halo" refers to fluoro, chloro and bromo.

"Pharmaceutically acceptable acid addition salt" means those salts which retain the spermicidal properties of the free bases and which are neither biologically or otherwise undesirable, formed with, for example, inorganic acids such as hydrochloric acid, hydrobromic acid, sulfuric acid, nitric acid or phosphoric acid; or inorganic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Optionally substituted" means that the substrate may or may not be substituted in the phenyl or naphthyl moiety with 1-3 substituents selected from the group consisting of halo atoms, lower alkyl, lower alkoxy or trifluoromethyl.

Article of Manufacture

A. Configuration

The device of the invention herein is intended to be insertable into, and retained in, the vagina for extended time periods, easily removable, comfortable, and non-interfering with intercourse. It is designed to remain in the vagina between menstrual periods, and to be disposable at the end of each use; to be self-inserted (unlike intrauterine devices which must be inserted by a physician) and to be of non-critical dimensions, so that it need not be fitted by a physician (as is the case with diaphragms).

DESCRIPTION OF THE DRAWING

An exemplary embodiment of the configuration of the invention is a ring such as that shown in FIG. 1, which is 70–80 mm across and 4–10 mm in diameter, and flexible so as to be retained between the rear wall of the vagina and the upper edge of the pubic bone, as shown in FIG. 2. The insertion and removal of such a device may be done by hand by the user.

Another embodiment of the configuration of the invention, exemplified in FIG. 3, is a diaphragm, which is essentially similar to the above ring in dimensions, properties and usability, except that the ring supports a membrane of thin flexible material. As the effectiveness of the device herein-described does not depend on its attributes as a mechanical barrier, this embodiment of the invention does not require fitting by a physician, as is the case with diaphragms in general.

Figure 1:
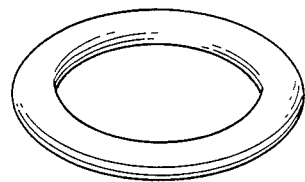
Figure 2:
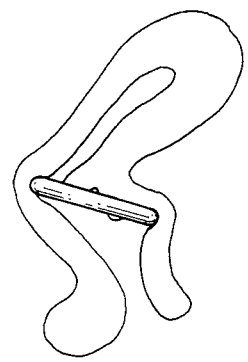
Figure 3:
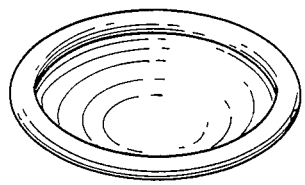
Figure 4:

Another preferred embodiment, exemplified in FIG. 4, is a cervical cap. As is the case with diaphragm, the efficacy of this embodiment of the device does not depend on its properties as a barrier. Therefore, exact fit is not critical, and user insertion is feasible. The cap is held in place by suction, and may be removed by hand.

Figure 5:

FIG. 5 shows a cross-section of a "diaphragm" which comprises a single molded piece of polymeric material which holds the spermicide in the matrix of the polymer.

The preceeding drawing depicts suitable embodiments of the device which are intended to be exemplary, and not limiting. Any device which consists as a whole, or in part, of a polymeric material capable of incorporating the spermicides and a pharmaceutically acceptable chelating agent described herein into the matrix of the polymer, and which will be retained in the vagina is encompassed by the invention.

B. Composition of the Matrix

The matrix which constitutes the structure and configuration of the device is composed of inert, flexible polymeric material which has been polymerized in the presence of, and as to include within itself, an effective amount of spermicide and a pharmaceutically acceptable chelating agent. The nature of the spermicide and a pharmaceutically acceptable chelating agent are further described hereinbelow. Additionally, if desired, polymerization may be carried out so as to incorporate other therapeutically active or contraceptive materials, as well as the spermicide, such as antifungal agents, antiviral agents, antibiotics, hormones, pH control agents, and the like.

Various types of polymers, such as polyethylene, polyurethane, nylon, and silastics are suitably flexible and inert. Preparation and regulation of the physical properties of said polymeric materials are well known to those skilled in the art. Standard methods of preparation and property control for these polymers may for example, be found in the *Modern Plastics Encyclopedia*, published by McGraw-Hill, New York, N.Y., U.S.A.

In the preferred embodiment, silastic polymers are employed, such as those described in U.S. Pat. No. 3,269,996. In a still more preferred embodiment, the silastic is a silicone elastomer such as Dow-Corning 382 silicone elastomer (available from Dow Corning Corp.), polymerized in the presence of a catalyst.

In a typical preparation, the spermicide 0.05%–10% by weight, preferably 0.5%–5% and a pharmaceutically acceptable chelating agent such as EDTA 0.05%–1% by weight, preferably 0.1%–0.75% are stirred into a paste containing the silicone elastomer and a suitable catalyst as essentially the balance of the mixture, and optionally, other therapeutically active or contraceptive ingredients. The mixture is placed into a mold suitable for the configuration such as those described above, and allowed to set. The proportion of catalyst to monomer will depend on the degree of flexibility desired, but will range from 10%–30% of the entire mixture, preferably about 20% for the uses described herein.

Optional additional therapeutically active or contraceptive ingredients may include, without limitation, bacteria controlling agents, such as, for example, penicillins, tetracyclines, or streptomycins or their pharmaceutically acceptable salts; antiinflammatory agents, such as, for example, cortisone or prednisolone or their salts; estrogens or other hormones, such as, for example, estradiol; prostaglandins; or progesterone; or physiologically safe acids such as tartaric, citric or boric, which serve to lower the ambient pH and thus create a hostile environment for spermatoza.

C. Spermicides

The effectiveness of the device and method of contraception described herein depends upon the use, as a spermicide, of compounds of the class consisting of the 1-substituted imidazoles.

Particularly useful classes of spermicides are 1-substituted imidazoles disclosed in U.S. Pat. No. 4,247,552 as well as the imidazoles described hereinbelow.

Illustrative of the classes of 1-substituted imidazoles forming a part of the present invention are those represented by the following general structural formula (as well as pharmaceutically acceptable acid addition salts thereof):

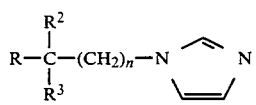
(I)

wherein:
(i)
R is alkyl of one to twelve carbon atoms, phenyl or phenyl-lower-alkyl of one to four carbon atoms wherein the phenyl ring is optionally substituted by one or more lower alkyl of one to four carbon atoms, lower alkoxy of one to four carbon atoms, halo or trifluoromethyl;

$R^2$ together with $R^3$ is ethylenedithio or propylenedithio wherein the alkylene chain is optionally substituted by one lower alkyl of one to four carbon atoms; and n is 1, 2 or 3;

(ii)
R is cycloalkyl of five to seven carbon atoms or cycloalkylalkyl of six to ten carbon atoms;
$R^2$ is hydrogen or lower alkyl of one to four carbon atoms;
$R^3$ is alkyl of two to twelve carbon atoms, cycloalkyl of five to seven carbon atoms or cycloalkylalkyl of six to ten carbon atoms; and n is 1, 2 or 3;

(iii)
R is phenyl or phenyl-lower-alkyl of one to three carbon atoms wherein the phenyl ring is optionally substituted by one or more lower alkyl of one to four carbon atoms, lower alkoxy of one to four carbon atoms, halo or trifluoromethyl;
$R^2$ is hydrogen or lower alkyl of one to four carbon atoms;
$R^3$ is alkyl of one to twelve carbon atoms, phenyl-lower-alkyl of one to three carbon atoms wherein the phenyl ring is optionally substituted by one or more lower alkyl of one to four carbon atoms, lower alkoxy of one to four carbon atoms, halo, or trifluoromethyl; and
n is 1, 2 or 3;

(iv)
$R_2$ is alkyl of one to twelve carbon atoms;
$R^2$ is hydrogen or lower alkyl of one to four carbon atoms;
$R^3$ is hydrogen or alkyl of one to twelve carbon atoms; and
n is 1, 2, 3 or 4; and (v)
R and $R^4$ are each alkyl of one to twelve carbon atoms, alkenyl of two to twelve carbon atoms, phenyl, phenyl-lower-alkyl of one to four carbon atoms or phenyl-lower-alkenyl of two to four carbon atoms wherein the phenyl ring is optionally substituted by one or more lower alkyl of one to four carbon atoms, lower alkoxy of one to four carbon atoms, halo, or trifluoromethyl;
$R^2$ is hydrogen or lower alkyl of one to four carbon atoms;
$R^3$ is X-$R^4$ wherein X is oxygen or sulfur; and
n is 1, 2 or 3.

Within group (i) it is preferred that R is an alkyl group of one to twelve carbon atoms. Within this subgroup it is preferred that R is alkyl of five to ten carbon atoms and n is 1 or 2. Within this subgroup it is preferred that $R^2$ together with $R^3$ is ethylenedithio. Particularly preferred are
1-[(3,3-ethylenedithio)-n-octyl]imidazole;
1-[(3,3-ethylenedithio)-n-decyl]imidazole;
1-[(3,3-ethylenedithio)-n-dodecyl]imidazole;
1-[(2,2-ethylenedithio)-n-octyl]imidazole;
1-[(2,2-ethylenedithio)-n-nonyl]imidazole;
1-[(2,2-ethylenedithio)-n-decyl]imidazole; and
1-[(2,2-ethylenedithio)-n-dodecyl]imidazole.

Within group (ii) it is preferred that R is cyclohexyl or cyclohexylalkyl. It is also preferred that when $R^3$ is alkyl that $R^3$ is alkyl of four to twelve carbon atoms. Particularly preferred are
1-(2-cyclohexylmethyl-n-hexyl)imidazole;
1-(2-cyclohexyl-n-hexyl)imidazole;
1-[2-methyl-2-(cyclohexylmethyl)-n-hexyl)imidazole;
1-[2-propyl-2-(cyclohexylmethyl)-n-pentyl]imidazole;
1-(3-cyclohexylmethyl)-n-heptyl)imidazole;
1-(4-cyclohexylmethyl)-n-octyl)imidazole; and
1-[2-cyclohexylmethyl)-3-cyclohexyl-n-propyl]-imidazole.

Within group (iii) it is preferred that R is phenyl-lower-alkyl optionally substituted by one or more lower alkyl of one to four carbon atoms, lower alkoxy of one to four carbon atoms, halo or trifluoromethyl. Preferred within this subgroup are
1-[2-(2-(2-chlorophenyl)ethyl)-n-hexyl]imidazole;
1-[2-(2-(4-chlorophenyl)ethyl)-n-hexyl]imidazole;
1-[2-(2-(4-methylphenyl)ethyl)-n-hexyl]imidazole;
1-(2-benzyl-n-heptyl)imidazole;
1-[2-(2-phenylethyl-n-octyl)imidazole; and
1-[2-(2-(4-methylphenyl)ethyl)-n-octyl]imidazole.

Within group (iv) it is preferred that R is alkyl of four to twelve carbon atoms. Particularly preferred are
1-(n-decyl)imidazole;
1-(n-dodecyl)imidazole;
1-(3-propyl-n-heptyl)imidazole;
1-(2-propyl-n-octyl)imidazole;
1-(4-n-butyl-n-octyl)imidazole; and
1-(3-n-pentyl-n-nonyl)imidazole.

Within groups (v) it is preferred that R is alkyl of three to eight carbon atoms. It is particularly preferred within this subgroup that $R^4$ is phenyl or phenyl-lower-alkyl wherein the phenyl ring is optionally substituted by one or more lower alkyl of one to four carbon atoms, lower alkoxy of one to four carbon atoms, halo or trifluoromethyl. Particularly preferred is
1-[2-(2,4-dichlorobenzyloxy)-n-octyl]imidazole.

Compounds of formula (I) as defined in group (i) are prepared by the methods disclosed in U.S. Pat. No. 4,359,475 incorporated herein by reference. Compounds wherein R is alkyl may be prepared by the above disclosed methods, but substituting the appropriate alkyl halo ketones for the aryl halo ketones. The alkyl halo ketones are prepared by the methods described in U.S. Pat. No. 4,078,071 and U.S. Pat. No. 4,359,475 using the appropriate alkyl starting material.

The compounds described in groups (ii), (iii) and (iv) are prepared, for example, by the following reaction sequence:

REACTION SEQUENCE

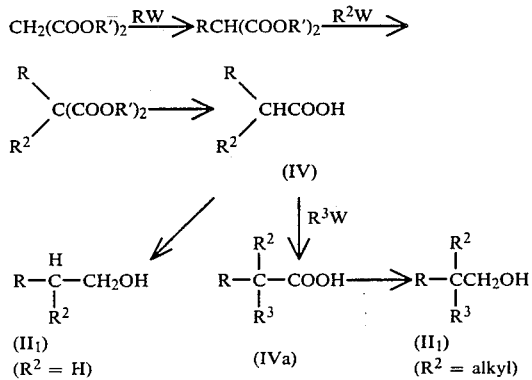

wherein R' is a lower alkyl group, e.g., an ethyl group, and R, $R^2$, and $R^3$, are as defined above and W is a leaving group.

In the above sequence, the alkylation steps may, of course, be carried out in any order, and either RW, $R^2W$, or $R^3W$ may be added first. The conversion of the acid of formula (IV) to the acid of formula ($IV_a$) wherein $R^2$ is lower alkyl may be carried out as depicted by employing a dianion (e.g., the dilithium derivative) of the acid of formula (IV), or by alkylation of an ester derivative of the compound of formula (IV) (e.g., a t-butyl ester) with $R^3W$ followed by hydrolysis. The required reaction conditions for the malonic ester synthesis are well-known to those skilled in the art and are described, for example, in *Organic Chemistry* by Robert T. Morrison and Robert N. Boyd (2nd ed.) pp. 918–921 and the *Merck Index* (9th ed.) p. ONR-57.

The compound of formula (IV) or ($IV_a$) is then reduced to the corresponding compound of formula (II) wherein n is 1, ($II_1$), using an appropriate reducing agent, such as, for example, borane-tetrahydrofuran complex or lithium aluminum hydride. The reducing agent, e.g., borane-tetrahydrofuran is added to a solution of the acid of formula (IV) or ($IV_a$) in a solvent such as tetrahydrofuran at $-20°$ to $30°$ C., preferably at $-0°$ to $10°$ C. and stirred for 5 minutes to 1 hour, preferably for 15 minutes to 30 minutes and then allowed to warm to room temperature.

Those compounds wherein $R^2$ and $R^3$ are both hydrogen may be prepared from $RCH(COOR')_2$ by decarboxylation followed by hydrogenation as described supra or directly from $RCH_2COOH$ by hydrogenation.

The intermediates of the formulas RW, $R^2W$ and $R^3W$ (wherein $R^2$ is lower alkyl) are commercially available, i.e. from Aldrich Chemical Co., or can be prepared by methods well known in the art. The hydroxy group of the corresponding alcohols may be converted to a suitable leaving group, W, by the methods described hereinafter, or the above intermediates may be prepared by methods analogous to the methods depicted in the above reaction sequence. Another method of preparing compounds RW or $R^3W$ wherein R and/or $R^3$ are cyclohexyl is by hydrogenation of the analogous phenyl compound by, e.g. catalytic hydrogenation, discussed hereinafter.

Compounds of formula (II) wherein n is greater than 1, may be prepared by homologation of compounds of formula ($II_1$).

The halide or sulfonate of the alcohol of formula ($II_1$) (n is 1) (i.e., compounds of formula III) is converted to the corresponding nitrile by reaction with, for example, sodium cyanide in dimethylformamide. The mixture is heated to $50°$ to $100°$ C., preferably to $60°$ to $90°$ C. for 1 to 24 hours, preferably overnight. The nitrile derivative is hydrolyzed by heating the reaction mixture to reflux for 1 to 24 hours, preferably overnight in the presence of a strong acid, e.g., aqueous sulfuric acid. Reduction as described above gives the alcohol of formula ($II_2$) This sequence can, of course, be repeated, resulting in a compound of formula II wherein n is 3 ($II_3$).

The conversion of compounds of formula (II) to compounds of formula (III) may be accomplished by treating a compound of formula (II) with either a halogenating agent, such as, for example, thionyl bromide or N-bromosuccinimide/triphenylphosphine or with an appropriate sulfonyl halide, for example, a sulfonyl chloride, optionally in an inert solvent, such as, for example, dichloromethane, or tetrahydrofuran in the presence of a base, for example, a tertiary amine, such as, for example, pyridine or triethylamine. The base may also be used as the solvent, for example, pyridine. The reaction is carried out at a temperature of about $-20°$ C. to about $50°$ C., preferably $0°$ C. to $25°$ C. and over a period of 5 minutes to 24 hours preferably, 30 minutes to overnight. Thereafter, the compound of formula (III) is converted to the final product of formula (I), by treating compound of formula (III) with at least one mole of imidazole per mole of compound of formula (III), preferably an excess (e.g. 1.1 to 5 moles imidazole per mole of compound of formula (III)). The reaction takes place in the absence of solvent (above the melting point of the mixture) or in an inert organic solvent such as dimethylformamide (DMF), acetonitrile, tetrahydrofuran, dimethylsulfoxide (DMSO) and the like; preferably, dimethylformamide, at a temperature between about $0°$ to $170°$ C., most preferably from about $50°$ to $150°$ C. Alternatively, the reaction may be carried out using a salt of imidazole, for example, an alkali metal salt, preferably a sodium salt, in the same solvents, at a temperature from about $0°$ to $150°$ C., preferably from about $20°$ to about $110°$ C.

The compound of formula (I) wherein R and/or $R^3$ is cyclohexyl may also be prepared by catalytically hydrogenating the corresponding phenyl imidazole compound wherein the phenyl ring is optionally substituted by lower alkyl. This compound, dissolved in an inert solvent, is hydrogenated using a catalyst such as rhodium on alumina at a pressure of about three to four atmospheres and a temperature of about $60°$ to $80°$ C.

Compounds of formula (I) as defined in group (v) are prepared according to the methods described in U.S. Pat. Nos. 3,658,813, 3,717,655, 3,839,574, 4,045,568, 4,055,652, 4,059,705, 4,078,071, 4,123,542, 4,213,991 all patents incorporated herein by reference.

Chelating Agents

The compounds having chelating action and useful as efficacy promoters in this invention were investigated by incorporating the chelating agent in, for example, a vaginal ring containing a 1-substituted imidazole in order to examine increase or decrease of spermicidal/spermatostatic activity of the 1-substituted imidazole. The mechanism of promotion effect has not so far been clarified, but it seems likely that the absorption mechanism of the cervical mucus may be changed through the chelating action and affinity to the mucous membrane possessed by these efficacy promoters. Although the mechanism of action of the efficacy promoter to increase the absorption by the cervical mucus may be speculated as mentioned above such a mechanism action is still no more than mere estimation and it is only sufficient to employ a compound having chelating action capable of bonding to at least calcium ions or magnesium ions. More specifically, the chelating ligands with effective chelating action, may be, for example, acid groups such as carboxylic acid group, sulfonic acid group, and phosphoric acid group, phenolic hydroxyl group, hydroxyl group, imino group, carbonyl group, amino group, and the like. Further, compounds having chelating action with these chelating ligands, include organic compounds having at least one acid group, such as carboxylic acid groups, thiocarboxylic acid groups, sulfonic acid groups or phosphoric acid groups, organic acid compounds having in addition, phenolic hydroxyl groups or organic compounds having at least 2 carbonyl groups. Organic compounds having at least one carboxylic acid group, sulfonic acid group or phosphoric acid group, include such compounds as monocarboxylic-, sulfonic-phosphoric-compounds or keto-carboxylic-, sulfonic-, phosphoric-compounds having carbonyl groups, hydroxy- or amino-carboxylic-, sulfonic-, phosphoric-compounds having hydroxyl groups or amino groups and polyacid compounds having two or more carboxylic acid groups, sulfonic acid groups or phosphoric acid groups. These compounds may also be classified as aliphatic compounds, alicyclic compounds, aromatic compounds and heterocyclic compounds. Further, keto-enol type tautomeric isomers may be classified either as compounds having carbonyl groups or as compounds having hydroxyl groups. Examples of chelating agents encompassed by this invention are polyacid compounds such as oxalic acid, malonic acid, succinic acid, fumaric acid, aconitic acid, pimellic acid, sebacic acid, suberic acid, azelaic acid, acridinic acid, allylmalonic acid, mesaconic acid, brassylic acid, dodecanolic acid, methylmalonic acid, ethylmalonic acid, phthalic acid, terephthalic acid, homophthalic acid, phenylsuccinic acid, phenylmalonic acid, phenylenediacetic acid, 1,3-naphthalenedicarboxylic acid, iminodiacetic acid, β-alaninediacetic acid, hydrochelidonic acid, 1,2-cyclohexanedicarboxylic acid, anthranylinoacetic acid, oxanylic acid-o-carboxylic acid, tricarballylic acid, 1,3-diamino-propanetetraacetic acid, hydroxyethyliminodiacetic acid, ethylenediaminediacetic acid, ethylenediaminedipropionic acid, hydroxyethylethylenediaminetriacetic acid, ethylenediaminetetraacetic acid, trans-cyclohexanediamine-tetraacetic acid, diaminopropanoltetraacetic acid, diethylenetriaminepentaacetic acid, ethylenediamine-di-o-hydroxyphenylacetic acid, triethylenetetraminehexaacetic acid, nitrilotriacetic acid, nitrilotripropionic acid and the like. Examples of hydroxy-acid compounds or phenolic hydroxyl group-acid compounds are lactic acid, citric acid, isocitric acid, malic acid, glyceric acid, tartaric acid, oxyacetic acid, dihydroxylethylglycinepantothenic acid, pantoic acid, mevalonic acid, iduronic acid, saccharic acid, phospheneolpyruvic acid, 2-phosphoglyceric acid, 3-phosphoglyceric acid, glycero-3-phosphoric acid, glucose-1,6-diphosphoric acid, fructose-1,6-diphosphoric acid, α-oxybutyric acid, 8-oxybutyric acid, gluconic acid, α-oxyisobutyric acid, glucuronic acid, galacturonic acid, leusinic acid, oxyglutamic acid, diethooxalic acid, strolactinic acid, phenyllactic acid, naphthylglycolic acid, phenylhydroacrylic acid, benzylic acid, mandelic acid, salicylic acid, 2,5-dihydroxybenzoic acid, 2,3-dihydroxybenzoic acid, 2,6-dihydroxybenzoic acid, tetra-oxyhexahydrobenzoic acid, shikimic acid, melilotic acid, hexahydrosalicyclic acid, o-, m-, p-phenolsulfonic acid, 1,2-hydroxybenzene-3,5-disulfonic acid, 1-naphthyl-2-sulfonic acid, 1-naphthol-3,6-disulfonic acid, 4-amino-phenol-2-sulfonic acid, and the like. Exemplary carbonyl-acid compounds are glyoxalic acid, glyoxylylactic acid, acetoacetic acid, oxaloacetic acid, a-ketobutyric acid, acetopyruvic acid, pyuruvic acid, α-ketoglutaric acid, β-ketoglutaric acid, α-ketomalonic acid, α-ketovaleric acid, β-ketovaleric acid, benzoylformic acid, benzoylglylcolic acid, benzoylpropionic acid, benzoylbutric acid, levulinic acid, β-ketocapric acid, phenylpyruvic acid, oxanylic acid, and the like. Typical examples of monoacid compounds are butyric acid, isovaleric acid, caproic acid, caprylic acid, capric acid, undecylic acid, lauric acid, myrystic acid, palmitic acid, stearic acid, eicosanic acid, arachidonic acid, linoleic acid, linolenic acid, phenylthioacetic acid, phenylpropionic acid, γ-phenylbutyric acid, acetylsalicyclic acid, anisic acid, phenylphosphoric acid and the like. A compound containing phenolic hydroxyl groups may be, for example, salicylic acid as mentioned above. Amino-acid compounds may include amino acids such as quinaldic acid, kynurenic acid, glycine, alanine, proline, hydroxyproline, phenylalanine, phenylglycine, tyrosine, cystine, cysteic acid, ε-aminocaproic acid, aspartic acid, glutamine, glutamic acid, leucine, isoleucine, serine, valine, threonine, methionine, p-hydroxyphenylglycine, alginine, tryptophan, hystidine, lysine, γ-carboxyglutamic acid, kynurenine and the like. Further, organic compounds having at least two carbonyl groups, may be preferably employed as enamine derivatives between amino acids (e.g. glycine, lysine, leusine, serine, phenylalanine, glutamic acid, thyrosine, phenylglycine, p-hydroxyphenyl-glycine, proline, hydroxyproline) and diketo compounds (e.g. acetylacetone, propionylacetone, butyroylacetone, 3-phenylacetylacetone, methylacetonacetate, ethylacetoacetate, ethyldiacetoacetate, propylacetoacetate, methoxyethylacetoacetate, ethoxyethylacetoacetate, diethyl ethoxymethylenemalonate, dibutyl ethoxymethylmalonate, and the like). In addition, the above diketo compounds per se may also be employed as absorption promoters. These absorption promoters are generally used in the form of alkali metal salts such as sodium salts or potassium salts, or ammonium salts, but they may also be esterified to the extent that water solubility is not impaired. In some of the absorption promoters, for example, polyacid compounds such as ethylenediamine-tetraacetic acid (EDTA) or ethyleneglycol-bis(β-aminoethyl ether)N,N'-tetraacetic acid (EGTA), a part of the acid groups may be protected by esterification or be converted to other derivatives. In particular, in case of EDTA, one of the carboxylic groups may be converted to ethylester.

It is preferred that the chelating agent is selected from the group consisting of polyacid derivatives of ethylenediamine, enamine derivatives of amino acids, and compunds containing hydroxy or phenolic hydroxy group and carboxy groups. Particularly preferred are polyacid derivatives of etheylenediamine with ethylene-diaminetetraacetic acid (EDTA) being the most preferred.

Method of Contraception

The method of the present invention comprises effecting contraception using the article of manufacture described hereinabove. In this aspect of the invention, the device described herein is inserted and retained in the vaginal cavity in such a manner that an effective concentration of spermicide is maintained in the cervical mucus during and for at least 24 hours after removal of the device.

In the method of the present invention, the ability of the unique combination of the spermicide and pharmaceutically acceptable chelating agent to be absorbed by and maintained at effective levels in the cervical mucus permit insertion at any time during the menstrual cycle to as little as one hour before intercourse. Because the spermicide is absorbed at effective concentrations into the cervical mucus, the device of the present invention may be removed up to 24 hours prior to intercourse. This presents a distinct advantage over known devices and would be preferable to females with small vaginas and to partners who object to the presence of intrauterine devices during intercourse. An additional advantage of the present method of contraception is the sustained effective concentration of the spermicide in the cervical mucus for up to 24 hours after removal of the device. This provides greater freedom for the partners in that the protection is maintained during multiple coital acts.

The device of the present invention may be inserted, if so desired, at least as much as 36 days before intercourse and may be removed, if so desired, up to 24 hours before to immediately thereafter. It is contemplated that the device would be removed during menstruation, and that ordinarily its total residence time in the vagina would not be greater than one month. The device may be used repeatedly until the internal concentration of spermicide and chelating agent is decreased below an effective level.

The following examples are intended to illustrate, but not to limit, the invention:

EXAMPLE I

Six white, soft, elastic cervical rings were prepared, each of weight 0.5 g., outer diameter 2.3 cm, inner diameter 1.5 cm, and thickness 0.3 cm.

The rings were made from:
1-(2-(2,4-dichlorobenzyloxy)-n-octyl)imidazole malate: 0.01 g
EDTA: 2.5 mg
Dow Corning Silicone 382 elastomer: 0.6 g
Catalyst M (stannous octoate): 5 drops The procedure was as follows:

The spermicide and EDTA was mixed well with the elastomer, and to the resultant mixture was added the catalyst with thorough mixing with a spatula. The resultant paste was carefully transferred to molds by small increments to avoid trapping of air. The molds were then allowed to stand overnight at room temperature for the elastomer to cure, whereafter smooth white rings were obtained from the molds.

(Silicone 382 elastomer is an opaque viscous elastomer base composed of polydimethylsiloxane and silica filler.)

EXAMPLE II

A ring prepared as in Example 1 was placed intravaginally in a female stumptailed macaque (maintained in an estrogen-dominated physiological state by subcutaneously implanted silastic capsules of estradiol. Cervical mucus in such an animal continuously possesses the mucus characteristics only seen around the time of ovulation in normal macaques).

The ring was maintained in place for eight days, and then removed.

Twenty-four hours after ring removal, the female was mated, and poscoital analysis revealed the following:

|  | % Sperm Motility | Forward Progression |
| --- | --- | --- |
| Vaginal Fluid Sperm Conc. No. $\times 10^6$ |  |  |
| 158 | 70 | 4 |
| Cervical Mucus Sperm Con. (Per Grid) |  |  |
| 300 | 0 | 0 |

These results are indicative of the contraceptive effects achievable in the cervical mucus with devices according to the invention.

What is claimed is:

1. A contraceptive device which releases spermicide and a pharmaceutically acceptable chelating agent during intravaginal placement in a female mammal comprising
   (a) an inert, flexible polymeric material formed into a configuration suitable for vaginal insertion and long term retention in the vagina and permeable to the release of said spermicide and a pharmaceutically acceptable chelating agent;
   (b) an effective amount of a 1-substituted imidazole spermicide or the pharmaceutically acceptable acid addition salts thereof, included within the matrix of said polymeric material, the imidazole having the formula $$R-\underset{\underset{R^3}{|}}{\overset{\overset{R^2}{|}}{C}}-(CH_2)_n-N\underset{\underline{\quad\quad}}{\overset{\frown}{\quad\quad}}N \quad\quad (I)$$

wherein:
(i)
R is alkyl of one to twelve carbon atoms, phenyl or phenyl-lower-alkyl of one to four carbon atoms wherein the phenyl ring is optionally substituted by one or more lower alkyl of one to four carbon atoms, lower alkoxy of one to four carbon atoms, halo or trifluoromethyl;
$R^2$ together with $R^3$ is ethylenedithio or propylenedithio wherein the alkylene chain is optionally substituted by one lower alkyl of one to four carbon atoms; and n is 1, 2 or 3;

(ii)

R is cycloalkyl of five to seven carbon atoms or cycloalkylalkyl of six to ten carbon atoms;

$R^2$ is hydrogen or lower alkyl of one to four carbon atoms;

$R^3$ is alkyl of two to twelve carbon atoms, cycloalkyl of five to seven carbon atoms or cycloalkylalkyl of six to ten carbon atoms; and n is 1, 2 or 3;

(iii)

R is phenyl or phenyl-lower-alkyl of one to three carbon atoms wherein the phenyl ring is optionally substituted by one or more lower alkyl of one to four carbon atoms, lower alkoxy of one to four carbon atoms, halo or trifluoromethyl;

$R^2$ is hydrogen or lower alkyl of one to four carbon atoms;

$R^3$ is alkyl of one to twelve carbon atoms, phenyl-lower-alkyl of one to three carbon atoms wherein the phenyl ring is optionally substituted by one or more lower alkyl of one to four carbon atoms, lower alkoxy of one to four carbon atoms, halo, or trifluoromethyl; and n is 1, 2 or 3;

(iv)

R is alkyl of one to twelve carbon atoms;

$R^2$ is hydrogen or lower alkyl of one to four carbon atoms;

$R^3$ is hydrogen or alkyl of one to twelve carbon atoms; and n is 1, 2, 3 or 4; or (v)

R and $R^4$ are each alkyl of one to twelve carbon atoms, alkenyl of two to twelve carbon atoms, phenyl, phenyl-lower-alkyl of one to four carbon atoms or phenyl-lower-alkyl of two to four carbon atoms wherein the phenyl ring is optionally substituted by one or more lower alkyl of one to four carbon atoms, lower alkoxy of one to four carbon atoms, halo, or trifluoromethyl;

$R^2$ is hydrogen or lower alkyl of one to four carbon atoms;

$R^3$ and X-$R^4$ wherein X is oxygen or sulfur; and n is 1, 2 or 3; and (c) an effective amount of a pharmaceutically acceptable chelating agent.

2. The device of claim 1 wherein the configuration is that of a ring of suitable size to fit into the vagina.

3. The device of claim 1 wherein the configuration is that of a diaphragm of suitable size to fit into the vagina.

4. The device of claim 1 wherein the configuration is that of a cervical cap.

5. The device of claim 1 wherein the polymeric material is formed from silicone elastomer.

6. The device of claim 1 wherein said polymeric material is formed by polymerization carried out in the presence of an effective amount of the spermicide and an effective amount of a pharmaceutically acceptable chelating agent.

7. The device of claim 1 comprising (a) an inert, flexible polymeric material formed into a configuration suitable for vaginal insertion and long term retention in the vagina and permeable to the release of said spermicide and a pharmaceutically acceptable chelating agent;

(b) between 0.5% and 5% of the 1-substituted imidazole spermicide or the pharmaceutically acceptable acid addition salts thereof, included within the matrix of said polymeric material; and (c) between 0.1% and 0.75% of a pharmaceutically acceptable chelating agent.

8. A device of claim 7 wherein the pharmaceutically acceptable chelating agent is selected from the group consisting of polyacid derivatives of ethylenediamine, enamine derivatives of amino acids, and compounds containing hydroxy or phenolic hydroxy group and carboxy groups.

9. A device of claim 8 wherein the pharmaceutically acceptable chelating agent is a polyacid derivative of ethylenediamine.

10. A device of claim 9 wherein the pharmaceutically acceptable chelating agent is ethylenediaminetetraacetic acid.

11. The device of claim 10 wherein the spermicide is selected from the group consisting of
1-[(3,3-ethylenedithio)-n-octyl]imidazole;
1-[(3,3-ethylenedithio)-n-decyl]imidazole;
1-[(3,3-ethylenedithio)-n-dodecyl]imidazole;
1-[(2,2-ethylenedithio)-n-octyl]imidazole;
1-[(2,2-ethylenedithio)-n-octyl]imidazole;
1-[(2,2-ethylenedithio)-n-decyl]imidazole; and
1-[(2,2-ethylenedithio)-n-dodecyl]imidazole.

12. The device of claim 10 wherein the spermicide is selected from the group consisting of
1-(2-cyclohexylmethyl-n-hexyl)imidazole;
1-(2-cyclohexyl-n-hexyl)imidazole;
1-[2-methyl-2-(cyclohexylmethyl)-n-hexyl)imidazole;
1-[2-propyl-2-(cyclohexylmethyl)-n-pentyl]imidazole;
1-(3-cyclohexylmethyl)-n-heptyl)imidazole;
1-(4-cyclohexylmethyl)-n-octyl)imidazole; and
1-[2-cyclohexylmethyl)-3-cyclohexyl-n-propyl]-imidazole.

13. The device of claim 10 wherein the spermicide is selected from the group consisting of
1-[2-(2-(2-chlorophenyl)ethyl)-n-hexyl]imidazole;
1-[2-(2-(4-chlorophenyl)ethyl)-n-hexyl]imidazole;
1-[2-(2-(4-methylphenyl)ethyl)-n-hexyl]imidazole;
1-(2-benzyl-n-heptyl)imidazole;
1-[2-(2-phenylethyl-n-octyl)imidazole; and
1-[2-(2-(4-methylphenyl)ethyl)-n-octyl]imidazole.

14. The device of claim 10 wherein the spermicide is selected from the group consisting of
1-(n-decyl)imidazole;
1-(n-dodecyl)imidazole;
1-(3-propyl-n-heptyl)imidazole;
1-(2-propyl-n-octyl)imidazole;
1-(4-n-butyl-n-octyl)imidazole; and
1-(3-n-pentyl-n-nonyl)imidazole.

15. The device of claim 10 wherein the spermicide is 1-[2-(2,4-dichlorobenzyloxy)-n-octyl]imidazole.

* * * * *